United States Patent
Yamada et al.

(10) Patent No.: US 9,149,786 B2
(45) Date of Patent: Oct. 6, 2015

(54) IODINE ADSORBENT AND COLUMN FOR WATER TREATMENT USING IODINE ADSORBENT

(71) Applicants: Arisa Yamada, Kawasaki (JP); Yumiko Sekiguchi, Kawasaki (JP); Hideyuki Tsuji, Yokohama (JP)

(72) Inventors: Arisa Yamada, Kawasaki (JP); Yumiko Sekiguchi, Kawasaki (JP); Hideyuki Tsuji, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 546 days.

(21) Appl. No.: 13/677,015

(22) Filed: Nov. 14, 2012

(65) Prior Publication Data

US 2013/0118968 A1    May 16, 2013

(30) Foreign Application Priority Data

Nov. 16, 2011 (JP) ................................. 2011-250858

(51) Int. Cl.
*B01J 20/02* (2006.01)
*B01J 20/26* (2006.01)
(Continued)

(52) U.S. Cl.
CPC .............. *B01J 20/223* (2013.01); *B01J 20/265* (2013.01); *B01J 20/321* (2013.01); *B01J 20/3204* (2013.01); *B01J 20/3265* (2013.01); *C02F 1/288* (2013.01); *C07F 19/005* (2013.01); *C08F 20/14* (2013.01); *B01J 20/0211* (2013.01); *B01J 20/08* (2013.01); *B01J 20/10* (2013.01); *B01J 20/103* (2013.01); *B01J 20/3248* (2013.01); *C02F 1/285* (2013.01); *C02F 2101/006* (2013.01);
(Continued)

(58) Field of Classification Search
CPC ...... B01J 20/10; B01J 20/103; B01J 20/0211; B01J 20/265; B01J 20/223; B01J 20/3265; B01J 20/3248; C02F 1/288; C02F 2101/006; C02F 2101/12

See application file for complete search history.

(56) References Cited

U.S. PATENT DOCUMENTS

| 3,880,619 A | 4/1975 | Richardson et al. |
| 4,659,477 A | 4/1987 | Macedo et al. |

(Continued)

FOREIGN PATENT DOCUMENTS

| DE | 32 08 231 A1 | 9/1983 |
| DE | 40 30 991 A1 | 4/1992 |

(Continued)

OTHER PUBLICATIONS

Final Rejection issued by the Japanese Patent Office on Jan. 27, 2015, for Japanese Patent Application No. 2011-250858, and English-language translation thereof.

(Continued)

*Primary Examiner* — Melvin C Mayes
*Assistant Examiner* — James Corno
(74) *Attorney, Agent, or Firm* — Finnegan, Henderson, Farabow, Garrett & Dunner, L.L.P.

(57) ABSTRACT

An iodine adsorbent of an embodiment includes: a carrier modified with a functional group represented by a formula (1); and a silver ion supported on the carrier, (1)

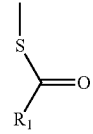

where $R_1$ is a polyol group.

7 Claims, 1 Drawing Sheet

(51) Int. Cl.
  B01J 20/22 (2006.01)
  C07F 19/00 (2006.01)
  C08F 20/14 (2006.01)
  B01J 20/32 (2006.01)
  B01J 20/10 (2006.01)
  B01J 20/08 (2006.01)
  C02F 1/28 (2006.01)
  C02F 101/00 (2006.01)
  C02F 101/12 (2006.01)

(52) U.S. Cl.
  CPC ....... *C02F2101/12* (2013.01); *C02F 2209/005* (2013.01); *C02F 2209/06* (2013.01); *Y10T 428/2989* (2015.01)

(56) References Cited

U.S. PATENT DOCUMENTS

| | | | |
|---|---|---|---|
| 4,902,665 A | | 2/1990 | Elfine |
| 5,220,058 A | * | 6/1993 | Fish et al. ............ 562/608 |
| 2007/0254044 A1 | * | 11/2007 | Karandikar et al. ......... 424/618 |

FOREIGN PATENT DOCUMENTS

| | | |
|---|---|---|
| FR | 2 797 786 | 3/2001 |
| JP | 2000-254446 | 9/2000 |
| JP | 2002-350588 | 12/2002 |
| JP | 2009-098083 | 5/2009 |
| WO | WO 2013/062044 A1 | 5/2013 |

OTHER PUBLICATIONS

Notification of the First Office Action issued by the State Intellectual Property Office of the People's Republic of China on May 20, 2014, for Chinese Patent Application No. 201210459258.9, and English-language translation thereof.

Matyas et al., "Functionalized Silica Aerogels: Advanced Materials to Capture and Immobilize Radioactive Iodine," Ceramic Materials for Energy Applications, Jan. 23-28, 2011, pp. 23-32.

Preliminary Examination Report issued by the French Patent Office on Jul. 5, 2013, for French Patent Application No. 1260930, and English-language translation of Written opinion portion thereof.

\* cited by examiner

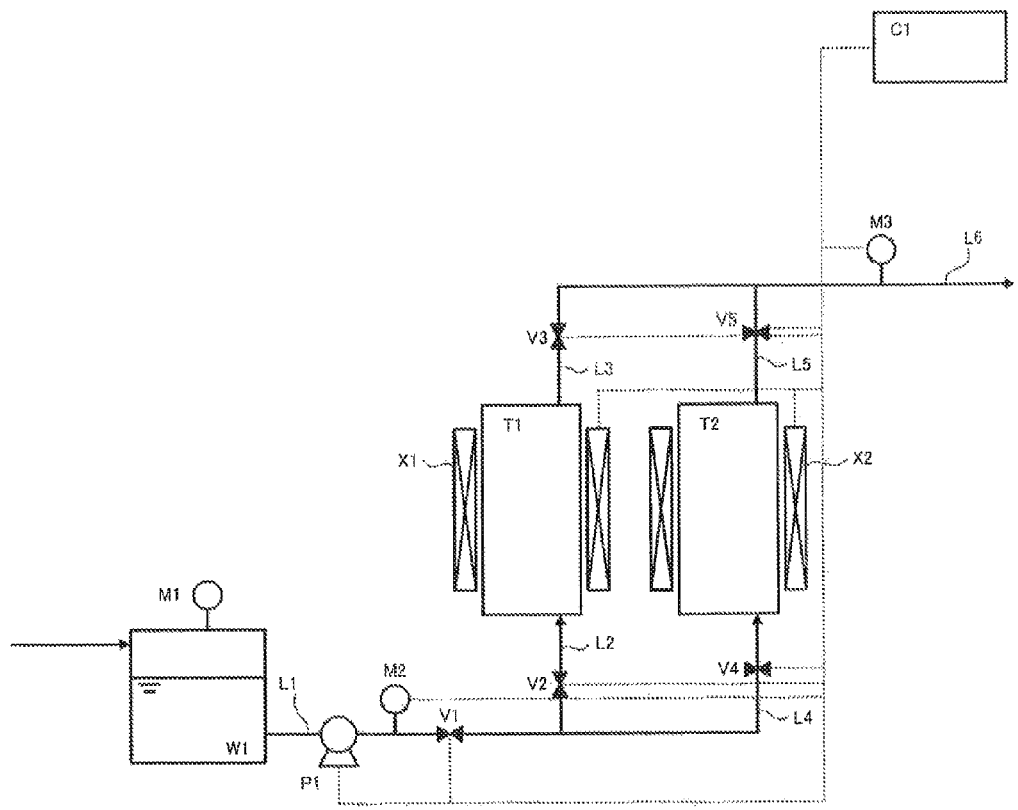

IODINE ADSORBENT AND COLUMN FOR WATER TREATMENT USING IODINE ADSORBENT

CROSS-REFERENCE TO RELATED APPLICATION

This application is based upon and claims the benefit of priority from Japanese Patent Application No. 2011-250858 filed on Nov. 16, 2011; the entire contents of which are incorporated herein by reference.

FIELD

Embodiments described herein relate generally to an iodine adsorbent, and a column for water treatment using an iodine adsorbent.

BACKGROUND

Due to the development of industry and increase in population, effective utilization of water resources has been required. Thus, reuse of waste water is very important. In order to achieve the effective utilization and reuse, it is necessary to purify the water, namely, to separate other substances from the water. As a method of separating other substances from liquid, various methods have been known, and there can be cited, for example, membrane separation, centrifugal separation, active carbon adsorption, ozonation, and aggregation, with which the removal of suspended solids or the like is conducted. Such methods make it possible to remove chemical substances such as iodine and nitrogen contained in water, which greatly affect on the environment, and to remove oil, clay and so on dispersed in water.

Meanwhile, in recent years, technologies of recovery and removal of iodine have been drawing an attention. A usage range of iodine is wide, and iodine is used in a wide range of fields such as a chemical field in which iodine is used in a chemical fiber and a thermal stabilizer, in addition to a medicinal field in which iodine is used in a disinfectant and the like. Iodine has many isotopes, in which iodine$^{131}$ ($^{131}$I) is a radioisotope, which is generated as a daughter nucleus when uranium$^{235}$ ($^{235}$U) undergoes fission.

Therefore, there is a case where the radioiodine is contained also in a radioactive material discharged in a large amount when a problem occurs in a nuclear power plant, and such radioiodine may be mixed in the air or in waste water. Therefore, the removal of radioiodine when the radioiodine is mixed in the air or in the waste water, has become a task.

As a method of removing iodine, there is a method of removing iodine by using an adsorbent in which, for example, silver is supported on zeolite, and calcium ions are eccentrically located on a peripheral portion of the resultant. In this case, it is possible to apply an apatite coating to a surface of the adsorbent, so that it is possible to suppress an elution of silver supported on zeolite from the adsorbent under a high temperature condition.

However, zeolite and silver are not firmly chemically bonded, so that there is a disadvantage that silver is eluted when a treated solution takes an acidic pH value, for example. Further, since zeolite is a powder with several μm and has a crystallinity, it is difficult to generate zeolite with a large particle size, and thus a size of the adsorbent to be obtained corresponds to a particle size of several μm, so that a handling is difficult, which is also a disadvantage. In order to solve the latter problem, it can be considered to perform granulation using a binder or the like, but, a new problem has arisen such that the number of manufacturing processes of the adsorbent increases, resulting in that a manufacturing cost of the adsorbent increases.

BRIEF DESCRIPTION OF THE DRAWINGS

FIG. 1 is a conceptual diagram of an iodine adsorption system in an embodiment.

DETAILED DESCRIPTION

An iodine adsorbent of an embodiment includes: a carrier modified with a functional group represented by a formula (1); and a silver ion supported on the carrier,

where $R_1$ is a polyol group.
(Iodine Adsorbent)

An iodine adsorbent of an embodiment has a predetermined carrier which is modified with a functional group represented by a formula (1),

where $R_1$ is a polyol group.

The functional group represented by the formula (1) forms thioester, and has a structure in which a polyol group is bonded, through substitution, to an end of a carbonyl group of thioester. It is known that a sulfur atom is firmly bonded to a metal ion through a coordinate bond, and further, it is known that a polyol group is also firmly bonded to a metal ion through a coordinate bond, so that when the carrier is modified with the functional group represented by the formula (1), it becomes possible to firmly bond a silver ion described below to the carrier.

Note that $R_1$ (polyol group) that forms the above-described functional group is preferably a polyol group with a carbon number of 5 or 6. Further, the above-described functional group is preferably a functional group represented by a formula (2).

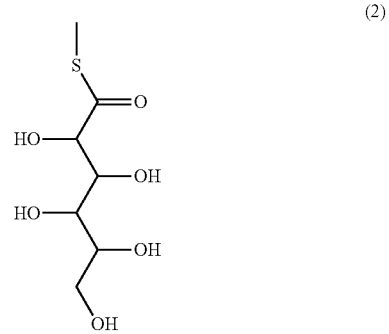

This depends on a type of cyclic sugar used when modifying the above carrier with the above functional group in a manufacturing method of the iodine adsorbent to be described below, and is a functional group obtained as a result of using cyclic sugar which is inexpensive and excellent in safety (gluconolactone, for example). Specifically, when the above carrier is modified with the functional group represented by the formula (2), it is possible to obtain the intended iodine adsorbent of the present embodiment inexpensively and under high safety.

The carrier preferably satisfies the following conditions (a) and (b). Specifically, the condition (a) is that the carrier itself has a sufficient strength, and can impart, to the iodine adsorbent, a strength which is high enough for practical use. The condition (b) is that the carrier has many hydroxyl groups on its surface, so that a percentage of modification of the carrier with the functional group represented by the formula (1) or the formula (2) through the manufacturing method to be described below, becomes high. Concretely, as the carrier, there can be cited silica ($SiO_2$), a metal oxide or the like.

Note that as the metal oxide, there can be cited titania ($TiO_2$), alumina ($Al_2O_3$), and zirconia ($ZrO_2$), or alkoxide, halide, and the like forming cobalt trioxide ($CoO_3$), cobalt oxide ($COO$), tungsten oxide ($WO_3$), molybdenum oxide ($MoO_3$), indium tin oxide (ITO), indium oxide ($In_2O_3$), lead oxide ($PbO_2$), PZT, niobium oxide ($Nb_2O_5$) thorium oxide ($ThO_2$), tantalum oxide ($Ta_2O_5$), calcium titanate ($CaTiO_3$), lanthanum cobaltate ($LaCoO_3$), rhenium trioxide ($ReO_3$), chromiumoxide ($Cr_2O_3$), ironoxide ($Fe_2O_3$), lanthanum chromate ($LaCrO_3$) barium titanate ($BaTiO_3$), and the like.

Note that among the aforementioned carriers, silica, titania, alumina, and zirconia are preferable since each of them has a high proportion of hydroxyl groups on the surface, resulting in that the percentage of modification with the functional group represented by the formula (1) or the formula (2) becomes high.

Further, it is also possible that the above carrier is set to an acrylic resin. The acrylic resin itself also has a sufficient strength, it can impart, to the iodine adsorbent, a strength which is high enough for practical use, and has an ester-bonded moiety. For this reason, through an ester exchange reaction, it is possible to realize high-percentage of modification with the functional group represented by the formula (1) or the formula (2), through substitution. Further, with the use of the acrylic resin, it is possible to synthesize a carrier having a glycidyl skeleton, so that it is possible to synthesize a carrier using glycidyl methacrylate or the like, for example, as a monomer, and to realize high-percentage of modification of the carrier with the functional group represented by the formula (1) or the formula (2).

Regarding a size of the carrier in the present embodiment, it is preferable that an average particle size is not less than 100 μm nor more than 5 mm. When the average particle size of the carrier is set to not less than 100 μm nor more than 5 mm, it is possible to realize both of a high filling percentage of the iodine adsorbent in a column and easiness of water-flow in the column, when performing adsorption of iodine, for example. When the average particle size is less than 100 μm, the filling percentage of the iodine adsorbent in the column becomes too high to reduce a proportion of gap, so that it becomes difficult to make water flow through the column. On the other hand, when the average particle size exceeds 5 mm, the filling percentage of the iodine adsorbent in the column becomes too low to increase gaps, resulting in that it becomes easy to make water flow through the column, but, since a contact area between the iodine adsorbent and waste water containing iodine is reduced, the percentage of adsorption of iodine achieved by the iodine adsorbent is reduced. The average particle size of the carrier is preferably not less than 100 μm nor more than 2 mm, and is more preferably not less than 300 μm nor more than 1 mm.

Note that in the iodine adsorbent of the present embodiment, the size of the adsorbent itself can be adjusted only by changing the size of the carrier, and accordingly, it can be understood that for obtaining an adsorbent whose handling is easy, it is only required to set the size of the carrier to a predetermined size. Specifically, it is possible to obtain an iodine adsorbent whose handling is easy, without performing operation such as granulation. Further, since there is no need to perform granulation or the like, it is possible to simplify a manufacturing process required for obtaining the iodine adsorbent whose handling is easy, resulting in that the reduction in cost can be realized.

The average particle size can be measured by a sieving method. Concretely, in accordance with JISZ8901: 2006 "powder for test and particle for test", it is possible to measure the average particle size by performing sieving using a plurality of sieves each having an opening of 100 μm to 5 mm.

In the iodine adsorbent in the present embodiment, the carrier is modified with the functional group represented by the formula (1) or the formula (2) through addition or substitution, and thereafter, a silver ion is supported on the carrier. The silver ion is supported when it is coordinate-bonded to the polyol group and sulfur of the functional group represented by the formula (1) or the formula (2), as described above.

Note that although it can be estimated that some kind of complex is formed when the silver ion is coordinate-bonded to an oxygen atom of the polyol group and a sulfur atom, under the present circumstances, the type of the complex is not clarified.

It can be considered that the silver ion that forms the iodine adsorbent in the present embodiment adsorbs iodine in waste water. Specifically, iodine exists in a form of anion such as iodine ion ($I^-$), iodide anion ($I^-$) or iodate ion ($IO_3^-$) in waste water. It can be considered that when such anion bonds to the silver ion in the iodine adsorbent through an ionic coordinate bond, the silver ion adsorbs iodine in the waste water.

Note that a formula (3) represents a conceptual diagram of an example of the iodine adsorbent of the present embodiment, and a formula (4) represents a conceptual diagram of an example of adsorption of iodine performed by the iodine adsorbent.

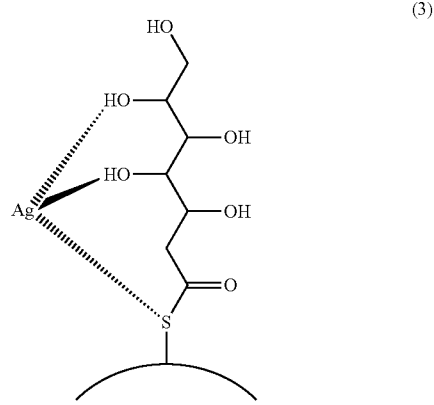

(3)

-continued

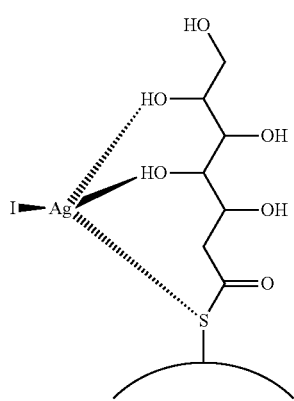

(4)

The formula (3) shows an example in which a polyol group with a carbon number of 6 is supported on a carrier, and represents an iodine adsorbent in which a silver ion is coordinate-bonded to oxygen atoms of the polyol group and a sulfur atom. Further, the formula (4) shows a state where, in waste water, iodine existed in the form of anion is adsorbed by being bonded to the silver ion in the iodine adsorbent through the ionic coordinate bond.

(Manufacturing Method of Iodine Adsorbent)

Next, a manufacturing method of the iodine adsorbent of the present embodiment will be described. Note that a manufacturing method to be described below is an example, and is not particularly limited as long as the iodine adsorbent of the present embodiment can be obtained.

First, the carrier such as silica or titania described above is prepared, and a surface of the carrier is subjected to treatment with a coupling agent having a thiol group, to thereby introduce the thiol group into the surface of the carrier. As the coupling agent having the thiol group, there can be cited a coupling agent such as sulfanylsilane such as γ-sulfanylpropyltrimethoxysilane or γ-sulfanylpropyltriethoxysilane, sulfanyl titanate, sulfanyl alumichelate, or sulfanyl zircoaluminate.

Regarding a reaction between the coupling agent and the carrier, there are a method in which the coupling agent is vaporized to be reacted with the carrier, a method in which the coupling agent is mixed in a solvent, and the mixture is mixed with the carrier to cause the reaction, and a method in which the coupling agent is directly brought into contact with the carrier without using the solvent to cause the reaction. When the reaction is caused in each of the methods, by performing heating, pressure reduction or the like, an amount (proportion) of thiol group introduced into the surface of the carrier can be adjusted.

Next, cyclic sugar lactone is reacted with the carrier into which the thiol group is introduced. Concretely, cyclic sugar lactone into which the thiol group is introduced is added to a predetermined solvent, and the resultant is heated, resulting in that an ester-bonded portion of the cyclic sugar lactone is ring-opened, and the thiol group and the ring-opened sugar lactone are reacted. Accordingly, the functional group represented by the formula (1) or the formula (2) is introduced into the carrier.

The reaction between the thiol group and the cyclic sugar lactone depends on the solvent to be used, a heating temperature, a reaction time and the like. The optimum heating temperature, reaction time and the like depend on the solvent to be used, so that optimum conditions are appropriately selected in accordance with the solvent to be used.

Note that as the cyclic sugar lactone, there can be cited gluconolactone, glucuronolactone, galactonolactone, galactoronolactone, mannonolactone, mannolactone, lyxonolactone, glucuronic acid or the like. By using such cyclic lactone, it is possible to make the aforementioned reaction with the thiol group proceed more securely.

Further, as the solvent, water, methanol, ethanol, n-propanol, isopropanol, acetone, tetrahydrofuran, n-hexane, cyclohexane, octane, and a mixture of those can be cited. Further, it is possible to add a catalyst or the like according to need. Also in this case, it is possible to make the aforementioned reaction with the thiol group proceed more securely.

Next, a silver ion is supported on the carrier obtained as described above. For example, there can be cited a method in which an aqueous solution is adjusted by using a predetermined reagent so that a concentration of silver becomes 0.1 mass % to 20 mass %, and then the above carrier is immersed in the aqueous solution and stirred, a method in which the above carrier is filled in a column, and the above aqueous solution is made to flow through the column, or the like.

Note that in the above-described manufacturing method, the coupling agent is used when introducing the thiol group into the surface of the carrier. On the contrary, it is also possible to obtain the iodine adsorbent without using the coupling agent. Specifically, the thiol group is fixed to the carrier by previously introducing a reactive functional group into the surface of the carrier, or by using a bifunctional cross-linking agent having a reactive group that reacts with the carrier and the thiol group, and thereafter, an operation same as the above operation is conducted.

As an example of the former, it is possible to introduce the thiol group into the surface of the carrier by introducing a glycidyl group into the surface of the carrier and causing a reaction between a moiety that reacts with the glycidyl group and a compound having the thiol group, or by introducing an ester bond into the surface of the carrier and causing a reaction of a compound such as ethanedithiol through ester exchange, or the like. As an example of the latter, there can be cited a method in which the thiol group is introduced into the surface of the carrier through ester exchange reaction or aminolysis by using 2-aminoethanethiol, 3-aminopropanethiol, 4-aminobutanethiol, 2-sulfanylethanol, 3-sulfanylpropanol, 4-sulfanylbutanol or the like.

(Method of Using Iodine Adsorption System and Iodine Adsorbent)

Next, explanation will be made on an adsorption system using the above-described iodine adsorbent and a method of using the adsorption system.

FIG. 1 is a diagram illustrating a schematic configuration of an apparatus used for adsorption of iodine in the present embodiment.

As illustrated in FIG. 1, in the present apparatus, columns for water treatment T1 and T2 filled with the aforementioned iodine adsorbent are disposed in parallel, and on lateral sides of the columns for water treatment T1 and T2, contact efficiency accelerators X1 and X2 are provided. The contact efficiency accelerators X1 and X2 can be provided as mechanical stirrers or non-contact magnetic stirrers, but, they are not essential components and thus can also be omitted.

Further, to the columns for water treatment T1 and T2, a waste water storage tank W1 in which waste water containing iodine is stored, is connected via waste water supply lines L1, L2 and L4, and the columns are connected to the outside via waste water discharge lines L3, L5 and L6.

Note that to the supply lines L1, L2, and L4, there are provided valves V1, V2, and V4, respectively, and to the discharge lines L3 and L5, there are provided valves V3 and V5, respectively. Further, to the supply line L1, a pump P1 is provided. In addition, to the waste water storage tank W1, the supply line L1 and the discharge line L6, concentration measuring units M1, M2 and M3 are respectively provided.

Further, the control of the aforementioned valves and pump, monitoring of measured values in the measuring units are collectively and centrally controlled by a controller C1.

Next, explanation will be made on the adsorption operation of iodine using the apparatus illustrated in FIG. 1.

First, waste water is supplied from the tank W1 to the columns for water treatment T1 and T2 through the waste water supply lines L1, L2 and L4 using the pump P1. At this time, iodine in the waste water is adsorbed in the columns for water treatment T1 and T2, and the waste water after the adsorption is performed is discharged to the outside through the waste water discharge lines L3 and L5.

At this time, it is possible to enhance the adsorption efficiency of iodine provided by the columns for water treatment T1 and T2, by driving the contact efficiency accelerators X1 and X2 according to need, to increase a contact area between the iodine adsorbent filled in the columns for water treatment T1 and T2 and the waste water.

Here, adsorption states of the columns for water treatment T1 and T2 are observed by the concentration measuring unit M2 and the concentration measuring unit M3 provided on the supply side and the discharge side, respectively, of the columns for water treatment T1 and T2. When the adsorption proceeds smoothly, the concentration of iodine measured by the concentration measuring unit M3 indicates a value lower than that of the concentration of iodine measured by the concentration measuring unit M2. However, as the adsorption of iodine in the columns for water treatment T1 and T2 gradually proceeds, a difference in the concentrations of iodine in the concentration measuring units M2 and M3 disposed on the supply side and the discharge side is decreased.

Therefore, when the value measured by the concentration measuring unit M3 reaches a previously set predetermined value, and it is judged that absorptivity of iodine of the columns for water treatment T1 and T2 reaches saturation, the controller C1 once stops the pump P1, closes the valves V2, V3 and V4, and stops the supply of waste water to the columns for water treatment T1 and T2, based on the information from the concentration measuring units M2 and M3.

Note that, although not illustrated in FIG. 1, when a pH of the waste water fluctuates, or the pH is strongly acidic or strongly alkaline and is out of a pH range suitable for the adsorbing material according to the present embodiment, it is also possible that the pH of the waste water is measured by the concentration measuring unit M1 and/or M2 and is adjusted through the controller C1.

After the absorptivity of iodine of the columns for water treatment T1 and T2 reaches saturation, the columns are appropriately changed with new columns for water treatment filled with the iodine adsorbent, and the columns for water treatment T1 and T2 in which the adsorption of iodine reaches saturation are appropriately subjected to necessary post-treatment. For example, if the columns for water treatment T1 and T2 contain radioiodine, the columns for water treatment T1 and T2 are broken into pieces, and then subjected to cement solidification or the like.

Note that although the adsorption system of iodine in the waste water using the columns for water treatment and the operation of the system, are explained in the above example, it is also possible to adsorb and remove iodine in exhaust gas by making exhaust gas containing iodine pass through the column as described above.

EXAMPLES

[Manufacture of Iodine Adsorbent]

Example 1

To 5 g of silica gel (average particle size of 210 μm), 8.7 g of γ-sulfanylpropyltrimethoxysilane and 20 ml of toluene were added, and refluxed for 9 hours. After that, the obtained solution was filtered, thereby obtaining a silica carrier modified with a thiol group. After the silica carrier was subjected to washing, 0.5 g of glucono-γ-lactone and 10 ml of methanol were added with respect to 0.5 g of the silica carrier, and refluxed for 6 hours. After the occurrence of reaction, the solution was filtered, and an obtained residue was subjected to water washing, to thereby obtain a silica carrier with a color ranging from white to yellow, which was derived from a reactant of the thiol group and glucono-γ-lactone and modified with a functional group including sulfur and a polyol group.

Next, 10 ml of aqueous solution containing 10 mass % of silver nitrate was added with respect to 0.5 g of the silica carrier obtained as described above, and the silica carrier was immersed in the aqueous solution for 1 hour at room temperature. After performing filtration, a residue was stirred in 20 ml of pure water, and after performing filtration, a residue was subjected to washing with water, thereby obtaining an iodine adsorbent.

Example 2

An iodine adsorbent was obtained in a similar manner to the example 1, except that glucono-γ-lactone was changed to L-mannono-1,4-lactone.

Example 3

An iodine adsorbent was obtained in a similar manner to the example 1, except that glucono-γ-lactone was changed to D-lyxono-1,4-lactone.

Example 4

An iodine adsorbent was obtained in a similar manner to the example 1, except that the coupling agent was changed from γ-sulfanylpropyltrimethoxysilane to γ-sulfanylpropylmethyldimethoxysilane.

Example 5

An iodine adsorbent was obtained in a similar manner to the example 1, except that the coupling agent was changed from γ-sulfanylpropyltrimethoxysilane to γ-sulfanylpropyltriethoxysilane.

Example 6

An iodine adsorbent was obtained in a similar manner to the example 1, except that the carrier was changed from silica gel to alumina.

Example 7

An iodine adsorbent was obtained in a similar manner to the example 1, except that the carrier was changed from silica gel to zirconia.

Example 8

An iodine adsorbent was obtained in a similar manner to the example 1, except that the carrier was changed from silica gel to titania.

Example 9

An iodine adsorbent was obtained in a similar manner to the example 1, except that the carrier was changed from silica gel to an acrylic resin, and that γ-sulfanylpropyltrimethoxysilane was changed to 2-aminoethanethiol. A synthesis of acrylic resin and thiol modification were conducted as follows. Methyl acrylate (monomer) and divinylbenzene (cross-linking agent) were subjected to suspension polymerization in water under the presence of sodium chloride and polyvinyl alcohol (dispersing agent), with azobisisobutyronitrile as an initiator. Accordingly, spherical particles with an average particle size of 300 μm were obtained. Note that the suspension polymerization was performed in water for 8 hours at 80° C.

After the completion of reaction, washing was performed for 24 hours at room temperature by using a mixed solvent in which ethanol and water were mixed at 80:20. To tetrahydrofuran, the obtained resin and 2-aminoethanethiol were added, and they were reacted for 6 hours under reflux, thereby obtaining a carrier having a thiol group on a surface thereof.

Example 10

An iodine adsorbent was obtained in a similar manner to the example 1, except that the carrier was changed from silica gel to an acrylic resin containing glycidyl group, and that γ-sulfanylpropyltrimethoxysilane was changed to 2-aminoethanethiol. A synthesis of acrylic resin and thiol modification are conducted as follows. Glycidyl methacrylate (monomer) and divinylbenzene (cross-linking agent) were subjected to suspension polymerization in water under the presence of sodium chloride and polyvinyl alcohol (dispersing agent), with azobisisobutyronitrile as an initiator. Accordingly, spherical particles with an average particle size of 300 μm were obtained. Note that the suspension polymerization was performed in water for 6 hours at 80° C. After the completion of reaction, washing was performed for 24 hours at room temperature by using a mixed solvent in which ethanol and water were mixed at 80:20.

Next, the obtained resin and 2-aminoethanethiol were added to tetrahydrofuran, and they were reacted for 6 hours under reflux, thereby obtaining a carrier having a thiol group on a surface thereof.

Example 11

An iodine adsorbent was obtained in a similar manner to the example 1, except that the average particle size of silica gel was changed to 12 μm.

Comparative Example 1

An aqueous solution containing 10 mass % of silver nitrate of 20 ml was added with respect to 1 g of zeolite (mordenite, Shin Tohoku Chemical Industry Co., Ltd.), and zeolite was immersed in the aqueous solution for 1 hour at room temperature. After performing filtration, a residue was stirred in 20 ml of pure water, and after performing filtration, a residue was subjected to washing with water, thereby obtaining a zeolite-based iodine adsorbent.

Comparative Example 2

IRA-458 (manufactured by Rohm and Haas Co.) being a commercially available strongly basic ion-exchange resin was used.

[Adsorption Test]

Tests of absorptivity were conducted using the iodine adsorbents obtained as described above. Potassium iodide of 580 mg was put in a 1 L measuring flask, and pure water was filled to a marked line of the flask to prepare an aqueous solution of potassium iodide of 600 ppm. Further, sodium chloride was added to a part of the above solution so that the concentration thereof became 3.5 mass %, to thereby prepare an aqueous solution of potassium iodide of 600 ppm containing 3.5 mass % of sodium chloride.

Next, 10 ml of test solution containing 600 ppm of iodine and 10 mg of adsorbent were added in a 10 ml centrifuge tube, and stirring was conducted in MIX ROTER for a certain period of time under room temperature and under a condition of 60 rpm. After the completion of reaction, the solution was filtered using a cellulose membrane filter with a pore size of 0.2 μm (RC-50).

Regarding a concentration of iodine in the filtrate, the concentration was determined in accordance with an iodine determination method of JIS. Concretely, 2 ml of solution of 30 mass % of hydrogen peroxide was added with respect to 200 μl of the filtrate and they were stirred, and thereafter, 200 μl of solution of 1 mass % of starch was added. After performing stirring, 2 ml of toluene was added and stirred, and it was confirmed that an organic layer was colored. The organic layer was taken out to be put in a cell made of quartz glass, an absorptiometer (U-2100, manufactured by Hitachi, Ltd.) was used in which zero adjustment was conducted at 800 nm, and the concentration was calculated from an absorbance at 300 nm. Unless particularly noted, an amount of adsorption corresponds to an amount of adsorption after the elapse of 1 hour from the start of the adsorption.

[Test Regarding Silver Ion Desorption]

In order to check whether the supported silver ion was not eluted from the carrier, each of the iodine adsorbents was immersed in an acidic aqueous solution and an aqueous solution with high salt concentration, thereby measuring a concentration of silver ion. As acid, sulfuric acid was used, and as salt, saturated sodium sulfate was used. Further, pH values of the respective solutions were set to 11 and 2. The adsorbent of 50 mg was added in 5 ml of each of the solutions, and after performing stirring, the presence/absence of silver in the aqueous solution was measured using a TBF color comparison method.

[Water-Flow Test in Column]

Each of the iodine adsorbents was filled in a 100 ml column made of glass, and 600 ml of test solution containing 20 ppm of iodine was made to flow through the column per 1 hour. Regarding the water-flow state, if the water flows smoothly, it is expressed by "G", and if the water does not flow smoothly, it is expressed by "NG".

Results of the aforementioned tests performed with respect to the adsorbents obtained in the examples 1 to 11 and the comparative examples 1 and 2 as described above, are presented in Table 1.

TABLE 1

| | TEST REGARDING SILVER ION ELUTION | | | IODINE ADSORPTION TEST | |
|---|---|---|---|---|---|
| | AQUEOUS SOLUTION OF SULFURIC ACID (ph2) | AQUEOUS SOLUTION OF SATURATED SODIUM SULFATE (ph7) | WATER-FLOW STATE IN COLUMN | CONCENTRATION OF REMAINING IODINE (ppm) | CONCENTRATION OF REMAINING IODINE (UNDER COEXISTENCE OF 3.5% OF SODIUM CHLORIDE)(ppm) |
| EXAMPLE 1 | ABSENCE OF ELUTION | ABSENCE OF ELUTION | G | 250 | 250 |
| EXAMPLE 2 | ABSENCE OF ELUTION | ABSENCE OF ELUTION | G | 266 | 260 |
| EXAMPLE 3 | ABSENCE OF ELUTION | ABSENCE OF ELUTION | G | 301 | 309 |
| EXAMPLE 4 | ABSENCE OF ELUTION | ABSENCE OF ELUTION | G | 245 | 241 |
| EXAMPLE 5 | ABSENCE OF ELUTION | ABSENCE OF ELUTION | G | 267 | 269 |
| EXAMPLE 6 | ABSENCE OF ELUTION | ABSENCE OF ELUTION | G | 349 | 342 |
| EXAMPLE 7 | ABSENCE OF ELUTION | ABSENCE OF ELUTION | G | 363 | 361 |
| EXAMPLE 8 | ABSENCE OF ELUTION | ABSENCE OF ELUTION | G | 328 | 237 |
| EXAMPLE 9 | ABSENCE OF ELUTION | ABSENCE OF ELUTION | G | 307 | 311 |
| EXAMPLE 10 | ABSENCE OF ELUTION | ABSENCE OF ELUTION | G | 289 | 293 |
| EXAMPLE 11 | ABSENCE OF ELUTION | ABSENCE OF ELUTION | NG | 224 | 230 |
| COMPARATIVE EXAMPLE 1 | PRESENCE OF ELUTION | PRESENCE OF ELUTION | G | 373 | 389 |
| COMPARATIVE EXAMPLE 2 | — | — | G | 116 | 468 |

As is apparent from Table 1, regarding the iodine adsorbents obtained in the examples, the elution of silver from each of the adsorbents in each of the aqueous solution of sulfuric acid and the aqueous solution of saturated sodium sulfate, was not confirmed. On the other hand, regarding the iodine adsorbent obtained in the comparative example 1, the elution of silver from the adsorbent was confirmed. From this, it can be understood that, in each of the iodine adsorbents obtained in the examples, silver is firmly bonded to the carrier by being coordinate-bonded to sulfur and the polyol group of the functional group with which the carrier is modified and, on the other hand, since the iodine adsorbent in the comparative example 1 uses zeolite as the carrier, a bonding strength of silver with respect to the carrier is weak.

Further, when the examples and the comparative example 1 are referred to, it can be understood that a concentration of remaining iodine in each of the examples is lower than that in the comparative example 1, and thus the iodine absorptivity is excellent in the examples. It can be considered that, one of the reasons thereof is that silver is eluted from the adsorbent in the comparative example 1 as described above.

Further, when the examples and the comparative example 2 are referred to, it can be understood that, although the ion-exchange resin in the comparative example 2 is excellent in absorptivity of iodine alone, the iodine absorptivity thereof is deteriorated when another component (sodium chloride in the present example) is contained in the aqueous solution. Therefore, it can be understood that each of the iodine adsorbents obtained in the examples can adsorb iodine, with high absorptivity, from waste water containing various substances.

Further, when the example 1 and the example 11 are compared, it can be understood that, in the example 11, the concentration of remaining iodine is also low and thus the iodine absorptivity is excellent, but, due to the small average particle size, there is an influence on the water-flow state in column. For this reason, it can be understood that when the iodine adsorbent is used concretely such that it is filled in the column, it is also required to take the average particle size of the iodine adsorbent into consideration.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An iodine adsorbent, comprising:
   a carrier modified with a functional group represented by a formula (1); and
   a silver ion supported on the carrier,

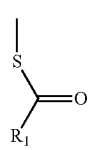

(1)

where $R_1$ is a polyol group.

2. The iodine adsorbent according to claim 1, wherein the functional group is represented by a formula (2).

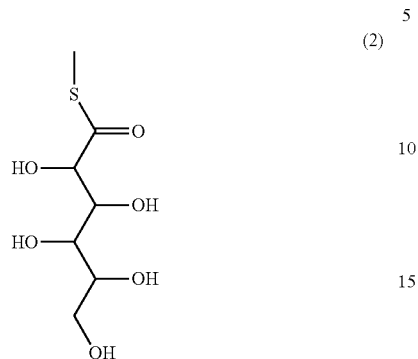

3. The iodine adsorbent according to claim 1, wherein, the carrier is silica.

4. The iodine adsorbent according to claim 1, wherein the carrier is at least one selected from the group consisting of titania, alumina, and zirconia.

5. The iodine adsorbent according to claim 1, wherein the carrier is an acrylic resin.

6. The iodine adsorbent according to claim 1, wherein the carrier has an average particle size being not less than 100 μm and not more than 5 mm.

7. A column for water treatment, comprising the iodine adsorbent according to claim 1 filled therein.

* * * * *